United States Patent
Appleby et al.

(10) Patent No.: US 6,391,035 B1
(45) Date of Patent: May 21, 2002

(54) HEMOSTATIC CLIP REMOVAL INSTRUMENT

(76) Inventors: Timothy Appleby, 105 Willesden Dr., Cary, NC (US) 27513; Matthew Rowland Shute, 3109 Carovel Ct., Raleigh, NC (US) 27612

( * ) Notice: Subject to any disclaimer, the term of this patent is extended or adjusted under 35 U.S.C. 154(b) by 0 days.

(21) Appl. No.: 09/534,684

(22) Filed: Mar. 24, 2000

(51) Int. Cl.⁷ .................. A61B 17/10; A61B 17/28
(52) U.S. Cl. ........................... 606/142; 606/207
(58) Field of Search ................ 606/157, 205, 606/207, 142

(56) References Cited

U.S. PATENT DOCUMENTS

| | | | |
|---|---|---|---|
| 3,326,216 A | 6/1967 | Wood | 606/142 |
| 4,187,712 A * | 2/1980 | Samuels et al. | 72/409.1 |
| 4,509,518 A | 4/1985 | McGarry et al. | 606/143 |
| 4,550,729 A * | 11/1985 | Cerwin et al. | 606/158 |
| 4,638,804 A * | 1/1987 | Jewusiak | 606/158 |
| 5,062,846 A | 11/1991 | Oh et al. | 606/142 |
| 5,100,416 A | 3/1992 | Oh et al. | 606/142 |
| 5,509,920 A | 4/1996 | Phillips et al. | 606/142 |
| 5,713,911 A * | 2/1998 | Recenet et al. | 606/157 |
| 6,099,536 A * | 8/2000 | Petillo | 606/142 |

* cited by examiner

Primary Examiner—Gary Jackson
(74) Attorney, Agent, or Firm—Mills Law Firm PLLC

(57) ABSTRACT

A surgical clip removal instrument having operative surfaces at the distal jaws that directly compress the legs of a latched surgical clip and upon limited closure movement differentially elongate the clip legs to achieve an unlatched condition. Upon release of the jaws, the inherent resiliency of the clip outwardly biases the legs while maintaining contact with the jaws, allowing removal of the clip from the surgical site in a single piece.

10 Claims, 3 Drawing Sheets

HEMOSTATIC CLIP REMOVAL INSTRUMENT

FIELD OF THE INVENTION

The present invention relates to surgical clip instruments and, in particular, to surgical instruments for removing polymeric hemostatic clips.

BACKGROUND OF THE INVENTION

Various types of hemostatic and aneurysm clips are used in surgery for ligating blood vessels to stop the flow of blood. Moreover such clips may be used for interrupting or occluding ducts and vessels in particular surgeries such as sterilization procedures. Generally, the clips are left in place until hemostasis or occlusion occurs.

Two types of clips, metal and plastic, have been preferred. Metal clips of alloys of stainless steel, titanium and tantalum are generally U-shaped or V-shaped. By means of a dedicated applier, the clip is permanently deformed over the vessel. An example of one such clip is disclosed in U.S. Pat. No. 5,509,920 to Phillips et al. An example of a metallic clip applied is disclosed in U.S. Pat. No. 3,326,216 to Wood wherein a forceps-type applier having conformal jaws is used to grip and maintain alignment of the clip during deformation. Such appliers may additionally dispense of plurality of clips for sequential application as disclosed in U.S. Pat. No. 4,509,518 to McGarry et al.

With the advent of high technology diagnostic techniques using computer tomography (CATSCAN) and magnetic resonance (MRI), metallic clips were found to interfere with the imaging techniques. To overcome such interference limitations, biocompatible polymers have been increasing used for surgical clips. Inasmuch as the plastic clip cannot be permanently deformed for secure closure, latching mechanisms have been incorporated into the clip design to establish closure conditions and secure against vessel opening. A particularly strong and secure plastic clip is disclosed in U.S. Pat. No. 5,062,846 to Oh et al. and assigned to the assignee of the present invention. Therein the plastic clip comprises a pair of curved legs joined at their proximal ends with an integral hinge and carrying at their distal ends interlocking latching members. Exemplary appliers for installing such clips are disclosed in U.S. Pat. No. 5,100,416 to Oh et al. and assigned to the assignee of the present invention. Therein, the distal ends of the clip include lateral bosses that are engaged by the jaws of the applier. Upon closure, the legs are pivoted inwardly about the hinge and contact and deflect the hook to allow reception of the locking tab.

While substantial advances have been made by the above and other approaches in the prior art for installing metal and polymeric clips, such instruments are solely dedicated to application and cannot be reversely operated to remove the clip once applied. Certain tools have been used for reversely deforming and removing metallic clips. However, a satisfactory instrument for removing latching polymeric clips has not been available. In instances where a surgeon desired to remove or relocate the clip, heretofore, the clip had to be physically severed by appropriate cutting instruments, such as scalpels, scissors and the like. Such removal techniques require substantial time and dexterity to remove safely the clip without adverse consequences to surrounding tissue. Accordingly, it would be desirable to provide a surgical instrument for removing plastic latching clips in a manner that releases the clip from a latched condition in a single piece without destruction of the clip and damage to surrounding tissue.

In view of the foregoing limitations, it is an object of the present invention to provide an effective instrument for removing polymeric surgical clips from a latched condition at the surgical site without physical destruction thereof.

Another object of the invention is to provide a surgical clip removal instrument for polymeric latching clips using non-destructive techniques and the inherent characteristics of the clip to achieve a released state at the surgical site for removal of the clip in a single piece.

A further object of the inventions is to provide a forceps-type surgical clip removal instrument that can be operated with simple closure movement to unlatch two-legged polymeric hemostatic clips directly at the surgical site.

BRIEF SUMMARY OF THE INVENTION

The foregoing objects and other advantages are achieved in the present invention by a surgical clip removal instrument having operative surfaces at the distal jaws that directly compress the legs of a latched surgical clip and upon limited closure movement differentially elongate the clip legs to achieve an unlatched condition. Upon release of the jaws, the inherent resiliency of the clip outwardly biases the legs while maintaining contact with the jaws, allowing the surgeon to remove the clip from the surgical site through withdrawal of the instrument thereby eliminating supplemental retrieval techniques and instruments.

More particularly, the removal instrument is of the forceps-type having a pair of elongated pivotal handles terminating with distal jaws. The instrument includes stop surfaces defining an open position and a closed position. The jaws have a stepped configuration including abutting surfaces adjacent the pivotal connection prescribing the closed position. Outwardly of the stop surfaces, the jaws terminate with low friction planar clip engaging surfaces lying in planes parallel to and spaced from the pivotal axis of the handles to establish a controlled width transverse gap. A cantilevered spring connected between the handles biases the jaws and through a slot and stop pin connection limits opening of the jaws in the normally open position. To remove a latched clip the jaws of the instrument are positioned to overly longitudinally the legs of the clip. Upon closing movement, the outer leg of the clip is flattened by one jaw increasing the longitudinal length thereof. At the opposed jaw, the clip hinge and latching hook are contacted and upon corresponding closure, the hinge and latching hook slide apart without changing the length of the other leg, gradually withdrawing the inner leg from the latched condition at the hook. After achieving an unlatched condition, further opening of the jaws allows the inherent resiliency at the hinge to outwardly pivot the legs to a fully released condition allowing removal of the clip in a single piece from the surgical site. Critical to the effective operation of the removal instrument is the aforementioned jaw spacing. If the gap is too wide in comparison with the latched height of the clip, the clip will not be sufficiently compressed to achieve the necessary differential leg lengths for unlatching. On the other hand, if the gap is too narrow, both legs will be compressively engaged precluding relative movement of the legs. Further, the planar jaws must have relatively low frictional characteristics for accommodating the necessary relative movements of the legs to the unlatched condition.

DESCRIPTION OF THE DRAWINGS

The above and other objects and advantages of the present invention will become apparent upon reading the following detailed description taken in conjunction with the accompanying drawings in which.

DETAILED DESCRIPTION OF THE PREFERRED EMBODIMENT

Figure 1:
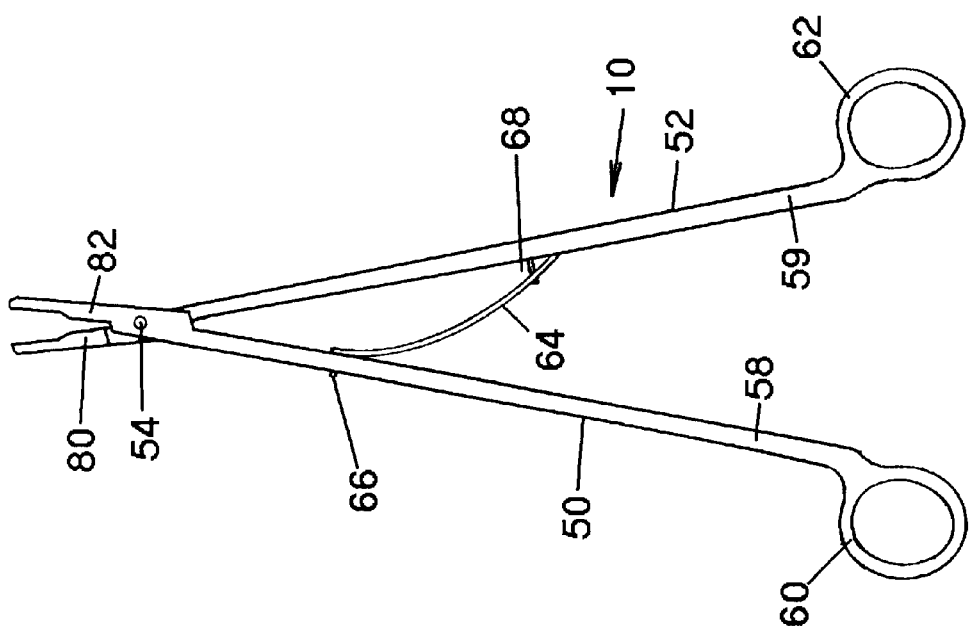
FIG. 1 is a plan view of a hemostatic clip removal instrument in accordance with the present invention.
Figure 5:
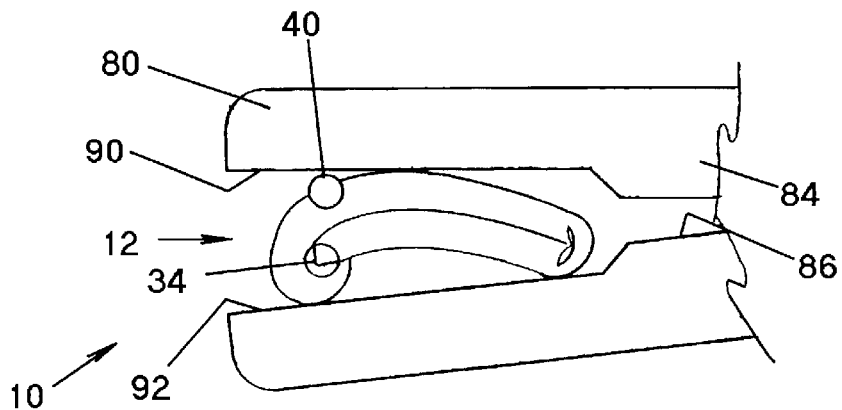
FIG. 5 is an enlarged fragmentary cross sectional view showing the hemostatic clip removal instrument engaging a hemostatic clip in a latched condition.
Figure 6:
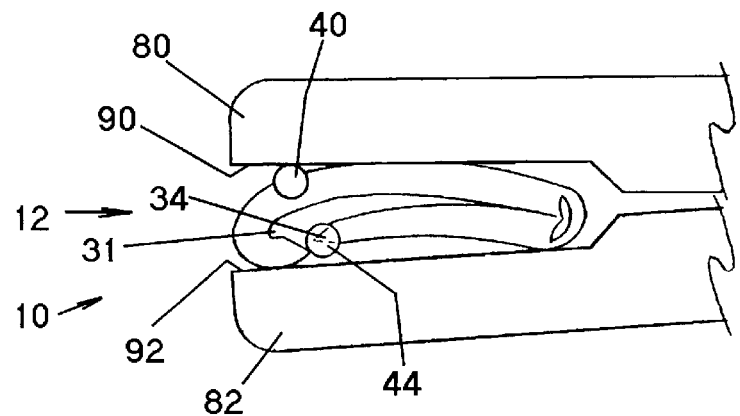
FIG. 6 is a view similar to FIG. 5 showing the hemostatic clip removal instrument conditioning the hemostatic clip to the unlatched condition.
Figure 7:
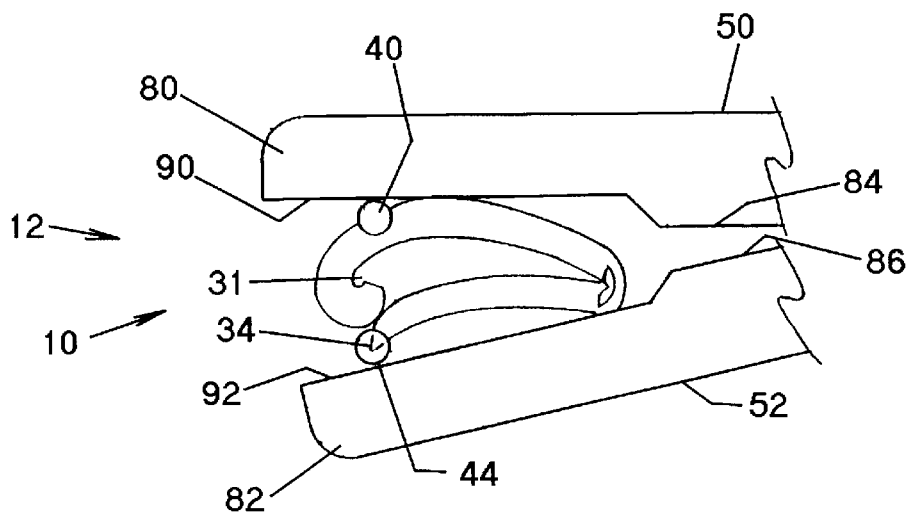
FIG. 7 is a view similar to FIG. 5 showing the hemostatic clip removal instrument holding the hemostatic clip in the released condition.

Referring to the drawings for the purpose describing the preferred embodiment only and not for limiting same, FIG. 1 shows a forceps-type ligating or hemostatic clip removal instrument 10 for removing a polymeric ligating or hemostatic clip 12 from the latched condition illustrated in FIG. 5, to the unlatched condition illustrated in FIG. 6, and to the released condition shown in FIG. 7. In such illustrated usage, the instrument 10 is effective for removing the clip 12 from a surgical operative position at the ligated end of a vessel after hemostasis or occlusion thereof, in a manner well known in the art.

Figure 8:
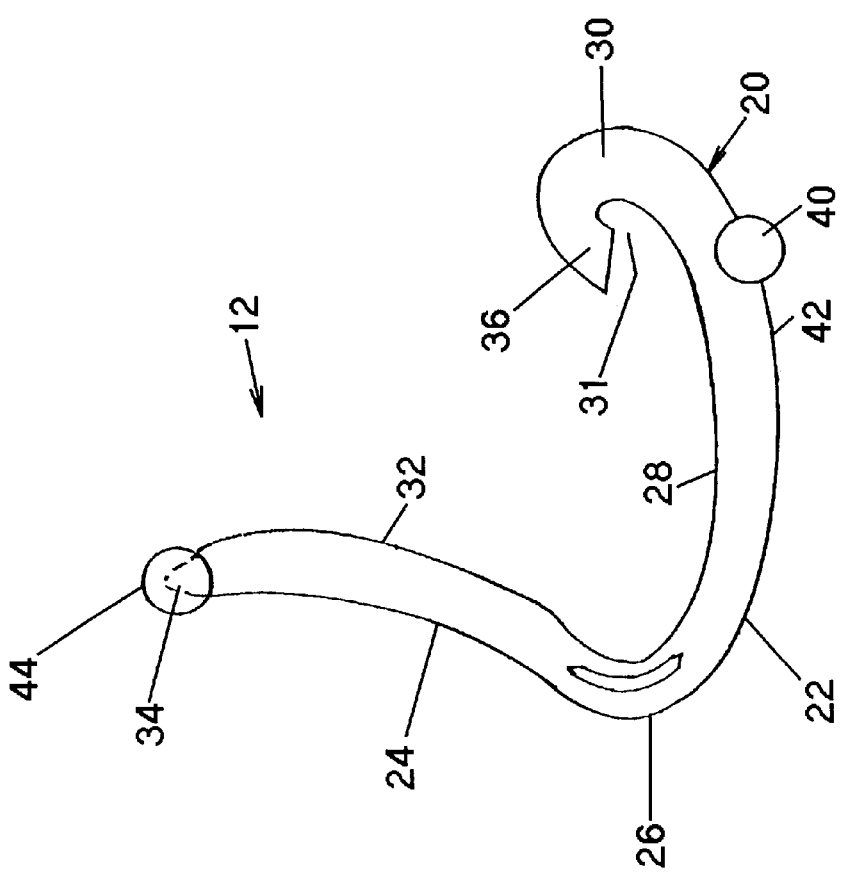
FIG. 8 is a side elevational view of a hemostatic clip for use with the hemostatic clip removal instrument of the present invention.

Referring to FIG. 8, the instrument 10 is particularly adapted for removal of polymeric hemostatic clips as described in U.S. Pat. No. 4,834,096 and will be described with reference thereto. Such a clip is representatively shown in FIG. 8. More particularly, the clip 12 comprises a one-piece integral polymeric body formed a suitable strong biocompatible engineering plastic of the type commonly used for surgical implants. Suitable examples include polyethylene terephthalate and polyoxymethylene, or other like thermoplastic materials that can be injection molded, extruded or otherwise processed into like articles.

The clip 12 comprises a one-piece body 20 having a first or outer leg 22 and a second or inner leg 24 joined at their proximal ends by an integral hinge 26. The outer leg 22 has a concave inner surface 28 transitioning to a curved, C-shaped hook 30 at its distal end defining a latching recess 31. The inner surface 32 of the inner leg 24 is convex and complementary to the concave inner surface 28 in the closed position, as shown in FIG. 5, whereby a vessels captured thereby will be completely occluded in use. The inner leg 24 has a pointed tip 34 at its distal end. As such the convex inner surface 32 and the concave inner surface 28 have matching radii of curvature. The hook 30 is distally reversely curved inwardly having a transverse beveled surface 36 defining with the concave inner surface 28 defining the recess 31 for conformally engaging the tip 34 in the latched condition.

Adjacent the distal end of the outer leg 22 and immediately inwardly of the hook 30, a pair of cylindrical bosses 40 are formed coaxially on the opposed lateral surfaces of the leg 22. The bosses 40 project outwardly beyond the convex outer surface 42 of the outer leg 22. At the distal end of the inner leg 24, a pair of cylindrical bosses 44 are formed coaxially on opposed lateral surfaces of the inner leg 24 at the tip 34 and extend longitudinally forwardly therebeyond. The bosses 40, 44 are engaged by an appropriate applicator instrument of the type described in the aforementioned U.S. Pat. No. 5,100,416 and pivoted inwardly thereby about the hinge portion 26 to engage the tip 34 at the end surface of the hook 30. Further pivotal movement of the applicator instrument longitudinally elongates the outer leg 22 and deflects the hook 30 allowing the tip 34 to align with the recess 31. Upon release of the applicator instrument, the tip 34 snaps into and is conformably seated in the recess 31, at a latched condition shown in FIG. 5, engaged between the surface 28 and surface 36, thereby securely clamping a designated vessel between surfaces 28, 32.

Referring to FIGS. 1 through 4, the hemostatic clip removal instrument 10 of the present invention serves to remove the clip 12 in the above latched condition from the vessel. The instrument 10 includes a pair of handles 50 and 52 that are pivotally connected at a transverse pin connection 54 for relative rotation about a transverse axis 56 between the open position illustrated in FIGS. 1 and 2, and the closed position illustrated in FIG. 4, and disposed in use in the intermediate operative positions shown in FIGS. 5 through 7. The handles 50, 52 include elongated shanks 58, 59 provided with conventional rings 60, 62 at the ends thereof for facilitating manual operation thereof. A cantilevered spring 64 is attached by a rivet 66 to the inner surface of the handle 50 and extends outwardly and rearwardly against the inner surface of the shank 59. The free end of the spring 64 is longitudinally slotted and retained by a headed fastener 68 on the shank 59 whereby the handles 50, 52 are biased toward the open position by the spring 64 and limited in outward pivotal movement by engagement of the fastener 68 at the end of the slot in the cantilevered spring 64.

Figure 4:
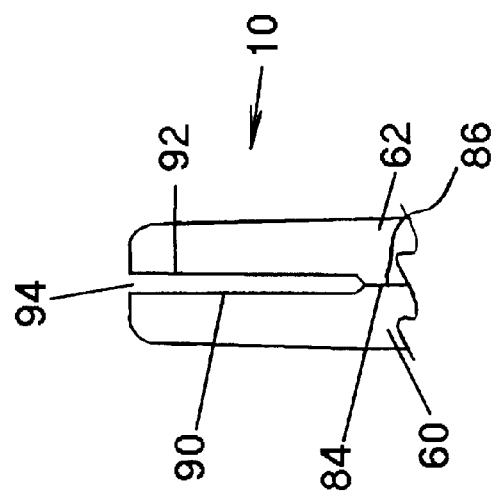
FIG. 4 is an enlarged fragmentary view of the jaws of the hemostatic clip removal instrument of FIG. 2 in the closed position.
Figure 3:
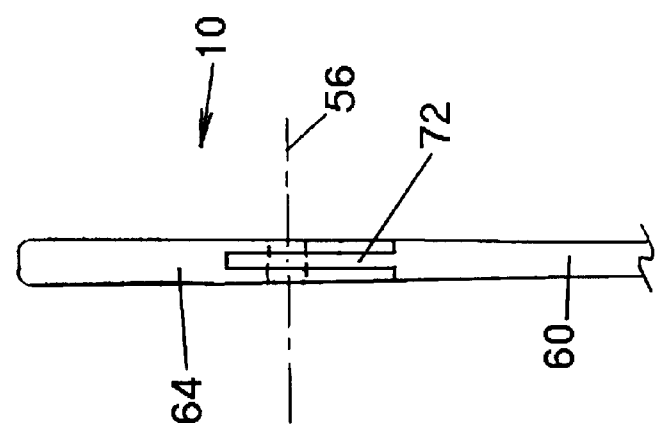
FIG. 3 is a fragmentary top view of the hemostatic clip removal instrument shown in FIG. 2.
Figure 2:
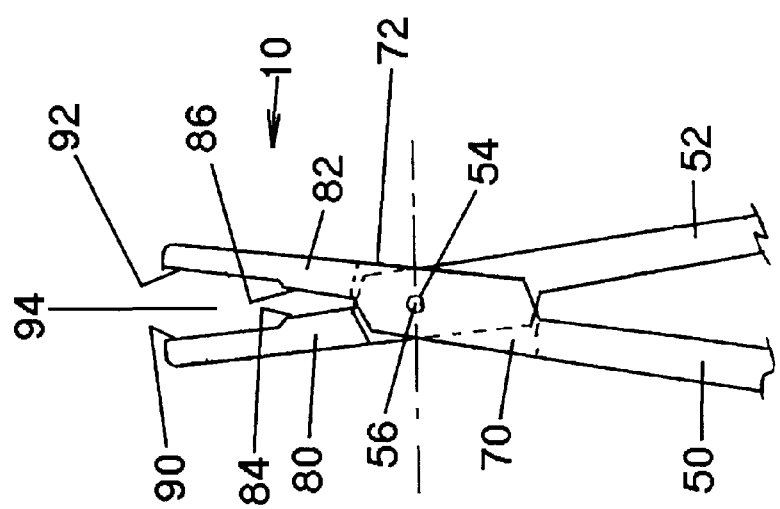
FIG. 2 is an enlarged fragmentary view of the jaws of the hemostatic clip removal instrument of FIG. 1 in the open position.

The handle 50 includes a transverse slot 70 adjacent the pin connection 54. The handle 62 includes laterally opposed slotted recesses establishing a central rib 72 disposed in the slot 70 for rotation about the pin connection 54. The handles 50, 52 include stepped jaws 80, 82 on the respective ends thereof immediately forwardly of the pin connection. The jaws 80, 82 include planar stop surfaces 84, 86, respectively lying in transverse planes intersecting the axis 56. The stop surfaces 84, 86 engage in the closed position. The outer ends of the jaws 80, 82 are provided with terminal clip engaging surfaces 90, 92 adjacent the stop surfaces 84, 86 and connected therewith by transverse transition surfaces. The clip surfaces 90, 92 lie in planes parallel to the stop surfaces 84, 86 and laterally spaced therefrom. In the closed position as shown in FIG. 4, the clip surfaces 90, 92 establish a constant width forwardly opening slot 94 in the closed position, equally spaced on either side of a median plane through the axis 56. As described below, the size of the gap or slot 94 with respect to the latched and unlatched height of the clip 12 is critical to the successful removal of the clip 12 from an associated vessel. If the gap is too large in comparison with the latched height of the clip, the clip is not sufficiently compressed to unlatch. If the gap is too narrow in comparison with the latched height of the clip, the legs are overly compressed preventing the differential elongation required to attain the unlatched condition. Further, in addition to correctly establishing the proper gap for the clip, it is also important that the clip surfaces have low frictional resistance to facilitate compression and elongation.

Preferably, the hemostatic clip removal instrument is formed of surgical grade stainless steel and the clip surfaces are planar and highly polished. Additionally, the instrument may be coated with a biocompatible plastic coating.

In use wherein a hemostatic clip is to be removed from a site, the surgeon will gain access to such site through appropriate surgical procedures exposing the clip. Thereafter, the instrument 10 is inserted over the clip 12 and longitudinally aligned therewith. Preferably the hinge 16 is adjacent the stop surfaces, 84,86. The jaws 80, 82 are closed against the biasing of the spring 64 until the top convex surface 42 of the outer arm 22 is engaged at the upper clip surface 90 and the hook 30 and the hinge 26 are engaged by the lower clip surface 92. In this position, it will be noted that the lower arm of the clip 12 is engaged only in the hinge area, the inner leg 24 is unrestrained, and the hook 30 is free to slide forwardly and pivot outwardly. Upon further closure of the handles, the upper arm 22 is flattened as the boss 40 and the upper leg 22 are engaged. During this compression, as a result of the polished, low friction surface characteristics of the clip surfaces, and the hook 30 slides forwardly and deflects upwardly with respect to the boss 44 and the hinge 26 slides rearwardly without a consequent lengthening of the lower arm 24. As a result the tip 34 is progressively withdrawn from the recess 31 and upon clearing the beveled surface 36 deflects to the unlatched condition shown in FIG. 6 under the inherent biasing of the compressed clip configuration. Upon further release, the clip begins to assume the open position as shown in FIG. 7. The instrument may be released to the fully open position and withdrawn. The released clip may then be removed from the site by conventional retrieval techniques.

As previously mentioned, the configuration of clip surfaces and the spacing therebetween in critical to the success in removing the clip. First the length of the clip surfaces 90, 92 should be provide ample, but not excessive, overlying of the clip 12 with sufficient width to accommodate angularity in alignment of the jaws 80, 82 with the clip. Further, the clip surfaces should be sufficiently low in frictional resistance to accommodate the differential movement during clip compression and resultant elongation. Moreover, the open condition of the jaws should allow for full reception of the clip without resistance to avoid significantly altering the clip location at the operative site. Furthermore, the width of the gap should provide sufficient compression to achieve the required upper arm elongation for unlatching. Excessive gap width will not provide the necessary flattening. Yet further, the gap should not be so narrow as to initiate significant compression of the lower arm 24 against the surface 92. Such conditions can exist with gaps too narrow and, as a result both arms are clamped between the surfaces preventing the differential elongation between the arms required for release. Accordingly, a compression of at least 25% is generally required and a gap of about 20% to 70% of the latched height is satisfactory and a gap of about 25% to 40% is preferred. By way of example, for a hemostatic clip of the above configuration having a free latched height of about 0.150 in. and an unlatching height of about 0.105 in. a gap of between 0.040 and 0.100 has been found to operate satisfactorily. As mentioned above, a low friction polished surface is preferred for the clip engaging surface and accordingly a surface finish of at least 63 RMS is preferred.

Having thus described a presently preferred embodiment of the present invention, it will now be appreciated that the objects of the invention have been fully achieved, and it will be understood by those skilled in the art that many changes in construction and widely differing embodiments and applications of the invention will suggest themselves without departing from the sprit and scope of the present invention. The disclosures and description herein are intended to be illustrative and are not in any sense limiting of the invention, which is defined solely in accordance with the following claims.

What is claimed:

1. A surgical clip removal instrument for removing a surgical clip having a pair of curved legs pivotally connected at their proximal ends by a hinge member and interconnected in a latched condition by locking means at their distal ends, said removal instrument comprising: a pair of elongated handles pivotally connected about a transverse axis and having a pair of jaws extending beyond said axis, said jaws having planar stop surfaces lying in a plane through said axis and abutting in a closed position; stop means associated with said handles for establishing an open position; a pair of planar clip engaging surfaces formed on said jaws adjacent said stop surfaces, said clip engaging surfaces being laterally offset from said stop surfaces and establishing a transverse gap therebetween in said closed position, said clip engaging surfaces adapted to engage said curved legs upon movement of said handles between said open position and toward said closed position whereby said legs are flattened sufficiently to disengage said latching means.

2. A surgical clip removal instrument for removing a two leg polymeric surgical clip from a vessel, said clip characterized by first and second legs having a curvature with abutting inner surfaces in a closed position and outer surfaces of differential lengths, said legs being pivotally connected at inner ends by an integral hinge member effective for biasing the legs to an open position, and including a deflectable hook member at the outer end of the first leg capturing and latching with a tab member at the outer end of said second leg in said closed position and released from the tab member when said curvature of said first leg is reduced, said removal instrument comprising:

a pair of elongated handles, each handle having a shank section and a jaw section;

means for pivotally interconnecting said handles intermediate said shank section and said jaw section for rotation of said jaw sections about a transverse axis between an open position and a closed position;

planar clip engaging surfaces on said jaw sections lying in planes laterally spaced from said transverse axis and defining a transverse gap in said closed position, one of said clip engaging surfaces engagable with said outer surface of said first leg and the other of said clip engaging surfaces engagable with said hinge means and said hook member, said clip engaging surfaces coacting on said clip member upon closing movement and effecting a reduction curvature of said first leg while accommodating sliding movement of said hook member and said hinge member, said reduction in said curvature and said sliding movement being sufficient to outwardly shift said hook member beyond said locking engagement and allowing said hinge member to bias said legs to a released condition for removal from said vessel.

3. The surgical clip removal instrument as recited in claim 2 including first stop means coacting with said jaw sections for establishing said closed position.

4. The surgical clip removal instrument as recited in claim 3 including second stop means coacting with said shank sections for establishing said open position.

5. The surgical clip removal instrument as recited in claim 2 wherein said gap is configured to compress said clip at least 25%.

6. The surgical clip removal instrument as recited in claim 5 wherein said gap in about 0.040 to 0.100 inch.

7. The surgical clip removal instrument as recited in claim 2 wherein said clip engaging surfaces have a polished finish.

8. A method of removing a polymeric surgical clip from a vessel wherein said surgical clip is characterized by first and second arcuate leg members joined at their proximal ends by a resilient hinge, said leg members having abutting inner surfaces engaging the vessel in a closed position and an opposite outer surfaces, the first leg member terminating at its distal end in a deflectable hook curved toward the second leg member and capturing the distal end of the second leg member in the closed position, said method of removing comprising the steps of:

a. engaging said opposite surface of said first leg member with a first planar surface;

b. engaging said hook and said resilient hinge with a second planar surface;

c. moving said first planar surface toward said second planar surface sufficiently to flatten said first leg member and retract said distal end of said second leg member from said hook whereby said resilient hinge outwardly biases said second leg member beyond said hook to an open position for removal of the surgical clip from the vessel.

9. The method as recited in claim 8 wherein said moving if effective to compress said clip at least 25% of the clip height in the closed position.

10. The method as recited in claim 9 including pivotally interconnecting said first planar surface and said second planar surface.

\* \* \* \* \*